(12) United States Patent
Angel

(10) Patent No.: US 10,123,865 B2
(45) Date of Patent: Nov. 13, 2018

(54) VASCULAR FILTER ASSEMBLY HAVING LOW PROFILE SHEATH

(75) Inventor: Luis F. Angel, San Antonio, TX (US)

(73) Assignee: Bio2 Medical, Inc., Golden, CO (US)

( * ) Notice: Subject to any disclaimer, the term of this patent is extended or adjusted under 35 U.S.C. 154(b) by 95 days.

(21) Appl. No.: 12/970,751

(22) Filed: Dec. 16, 2010

(65) Prior Publication Data

US 2012/0158037 A1   Jun. 21, 2012

(51) Int. Cl.
*A61M 29/00* (2006.01)
*A61F 2/01* (2006.01)

(52) U.S. Cl.
CPC ........ *A61F 2/013* (2013.01); *A61F 2002/016* (2013.01); *A61F 2230/008* (2013.01); *A61F 2230/0093* (2013.01)

(58) Field of Classification Search
CPC .... A61F 2/01; A61F 2/013; A61F 2230/0093; A61F 2230/008; A61F 2002/016
USPC ..................................... 606/1, 200, 159, 198
See application file for complete search history.

(56) References Cited

U.S. PATENT DOCUMENTS

| | | | | |
|---|---|---|---|---|
| 4,995,865 A * | 2/1991 | Gahara | ............ | A61M 25/0026 604/43 |
| 5,549,626 A * | 8/1996 | Miller et al. | ................... | 606/200 |
| 5,588,432 A * | 12/1996 | Crowley | ........................ | 600/439 |
| 5,776,140 A * | 7/1998 | Cottone | .................. | A61F 2/958 606/191 |
| 6,152,946 A * | 11/2000 | Broome et al. | ............... | 606/200 |
| 6,179,813 B1 * | 1/2001 | Ballow et al. | ........... | 604/164.01 |
| 6,290,710 B1 * | 9/2001 | Cryer | ..................... | A61F 2/013 606/159 |
| 6,361,545 B1 | 3/2002 | Macoviak et al. | ........... | 606/200 |
| 6,485,500 B1 * | 11/2002 | Kokish et al. | ................ | 606/194 |
| 6,537,294 B1 | 3/2003 | Boyle et al. | .................. | 606/200 |
| 6,706,053 B1 * | 3/2004 | Boylan et al. | ................ | 606/200 |
| 6,755,813 B2 | 6/2004 | Ouriel et al. | ................ | 604/537 |
| 6,997,938 B2 * | 2/2006 | Wang et al. | .................. | 606/200 |
| 7,399,308 B2 * | 7/2008 | Borillo et al. | ............... | 606/200 |
| 2002/0099407 A1 * | 7/2002 | Becker et al. | ............... | 606/200 |
| 2002/0123766 A1 | 9/2002 | Seguin et al. | ................ | 606/200 |
| 2003/0050663 A1 * | 3/2003 | Khachin | ............. | A61B 17/221 606/200 |
| 2003/0097094 A1 * | 5/2003 | Ouriel | .................... | A61F 2/013 604/93.01 |
| 2003/0097114 A1 * | 5/2003 | Ouriel et al. | ................. | 604/500 |
| 2004/0006368 A1 * | 1/2004 | Mazzocchi et al. | .......... | 606/200 |
| 2004/0006370 A1 | 1/2004 | Tsugita | ......................... | 606/200 |
| 2004/0133232 A1 | 7/2004 | Rosenbluth et al. | ......... | 606/200 |

(Continued)

OTHER PUBLICATIONS

International Search Report issued in corresponding foreign application, PCT/US2011/065538, pp. 1-6 (dated Aug. 22, 2012).

(Continued)

*Primary Examiner* — Richard Louis

(74) *Attorney, Agent, or Firm* — David G. Rosenbaum; Benjamin D. Rotman; Rosenbaum IP, P.C.

(57) ABSTRACT

A vascular filter assembly includes a catheter body having a self-expanding filter member coupled thereto. A sheath is disposed directly over the self-expanding filter member such that the self-expanding filter member is at least partially constrained from expansion in a first configuration within an interior space defined between the sheath and the catheter body. The sheath includes at least one aperture disposed through a wall thereof.

8 Claims, 6 Drawing Sheets

(56) References Cited

U.S. PATENT DOCUMENTS

| | | | | |
|---|---|---|---|---|
| 2004/0176794 | A1* | 9/2004 | Khosravi | A61F 2/013 606/200 |
| 2005/0149110 | A1* | 7/2005 | Wholey | A61F 2/013 606/200 |
| 2005/0159772 | A1* | 7/2005 | Lowe | A61F 2/01 606/200 |
| 2005/0234505 | A1* | 10/2005 | Diaz et al. | 606/200 |
| 2007/0060918 | A1 | 3/2007 | Holman et al. | 606/21 |
| 2008/0045895 | A1* | 2/2008 | Simpson et al. | 604/103 |
| 2008/0097296 | A1* | 4/2008 | Pepin | 604/103 |
| 2008/0097339 | A1 | 4/2008 | Ranchod et al. | 604/246 |
| 2008/0234723 | A1* | 9/2008 | Buiser et al. | 606/200 |
| 2009/0062840 | A1 | 3/2009 | Angel | 606/200 |
| 2009/0088790 | A1* | 4/2009 | Parodi et al. | 606/200 |
| 2009/0088791 | A1* | 4/2009 | Drasler | A61F 2/013 606/200 |
| 2009/0270974 | A1* | 10/2009 | Berez et al. | 623/1.17 |
| 2010/0217304 | A1 | 8/2010 | Angel et al. | 606/200 |

OTHER PUBLICATIONS

Written Opinion issued in corresponding foreign application, PCT/US2011/065538, pp. 1-6 (dated Aug. 22, 2012).

European Official Action issued in corresponding foreign application, pp. 1-4 (dated Nov. 19, 2014).

Bard Peripheral Vascular, "Simon Nitinol Filter Information Sheet" pp. 1-2.

Cook Medical, "Gunther Tulip Vena Cava Filter Retrieval Set for Jugular Vein Approach—Instructions for Use", pp. 1-5.

Cook Medical, "Gunter Tulip Vena Cava Filter Product Information Sheet", pp. 1-2.

Cordis, "OPTEASE Retrievable Vena Cava Filter Information Sheet", pp. 1-2.

Decousus, H., et al., "A clinical trial of vena caval filters in the prevention of pulmonary embolism in patients with proximal deep-vein thrombosis" *The New England Journal of Medicine*, 336(7): 409-415 (1998).

Lin, P.H., et al., "Vena caval filters in the treatment of acute DVT" *Endovascular Today*, pp. 40-50 (2005).

* cited by examiner

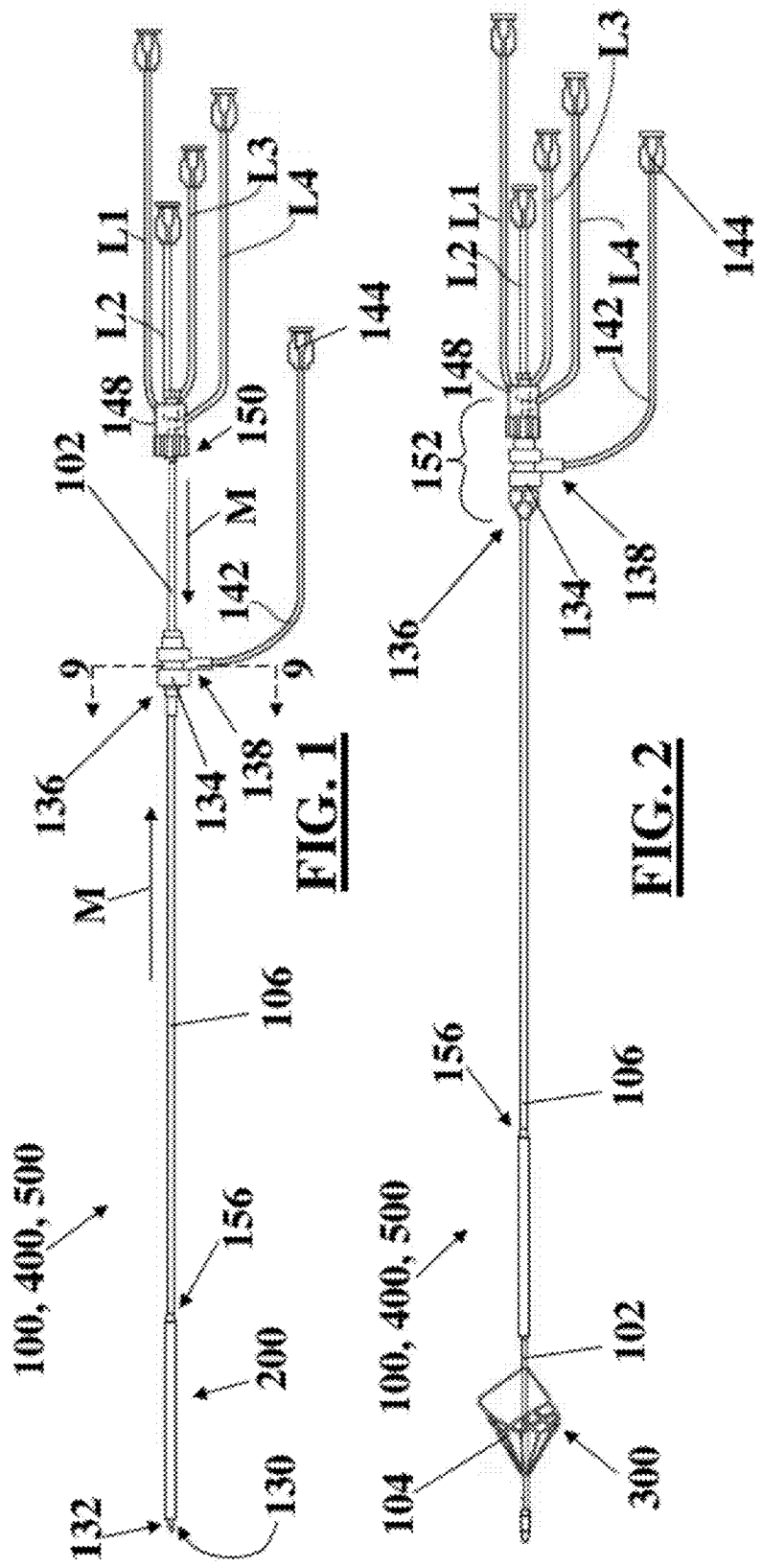

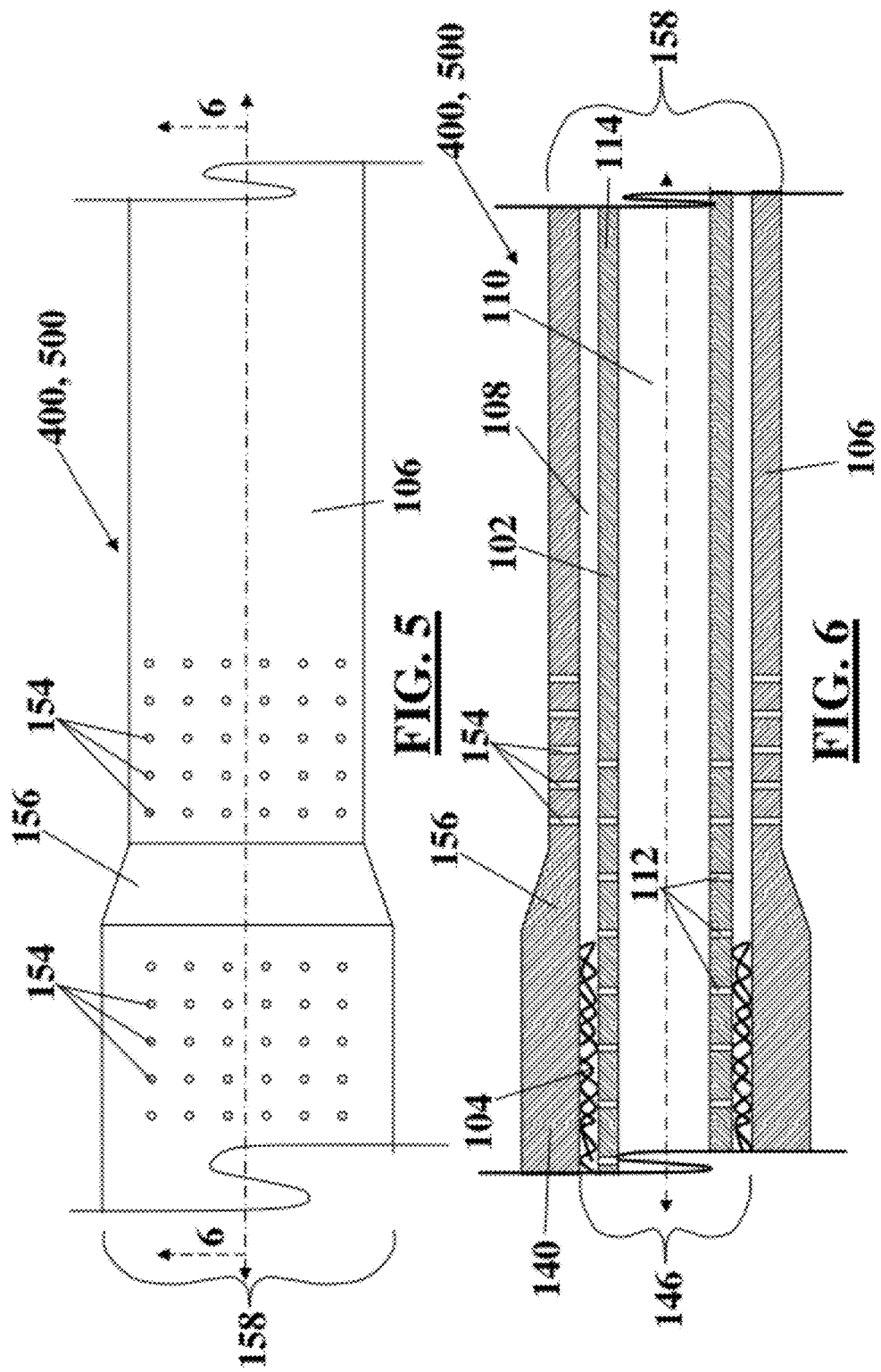

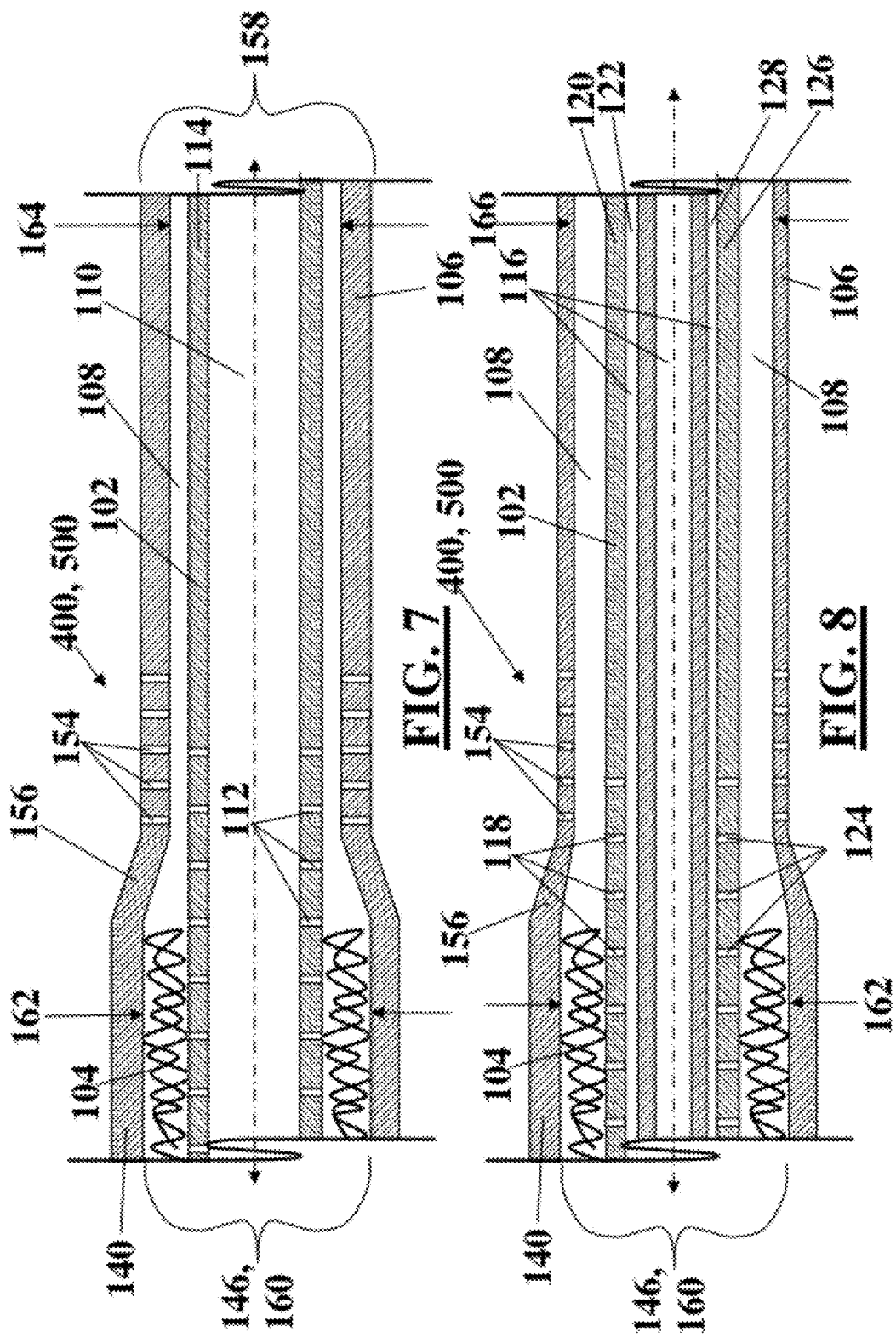

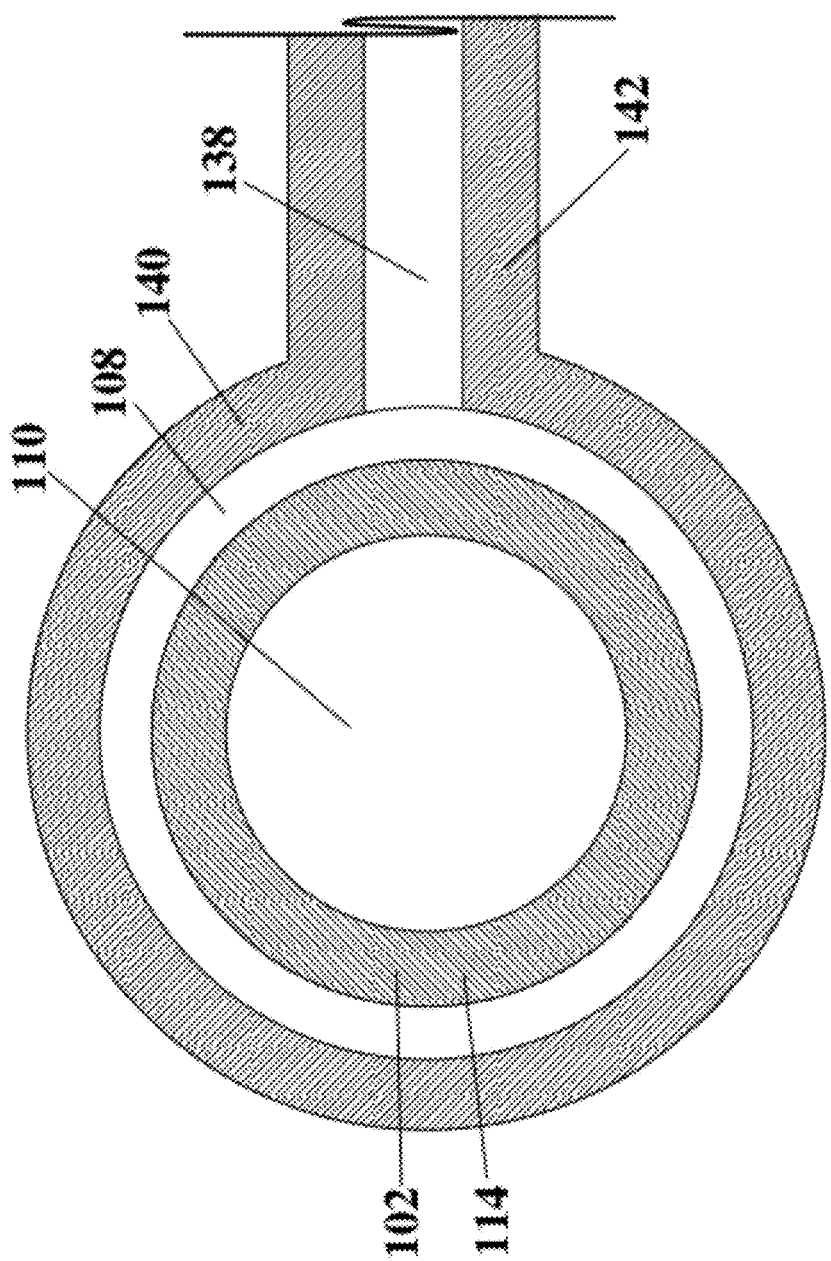

VASCULAR FILTER ASSEMBLY HAVING LOW PROFILE SHEATH

CROSS-REFERENCE TO RELATED APPLICATIONS

Not Applicable.

FIELD OF THE INVENTION

The present invention pertains generally to the field of vascular filters for capturing embolic material in the blood flow. More particularly, the present invention relates to a central access vena cava filter including a low profile constraining sheath having at least one port passing through the sidewall of the sheath.

BACKGROUND OF THE INVENTION

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. *A clinical trial of vena caval filters in the prevention of pulmonary embolism in patients with proximal deep-vein thrombosis. N Engl J Med* 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Günther Tulip (Cook Inc.), Opt Ease (Cordis Corp.), and Recovery nitinol filters (Bard Peripheral Vascular, Tempe, Ariz.) Lin P H, et al., *Vena caval filters in the treatment of acute DVT. Endovascular Today* 2005; January:40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates. Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

In addition to providing a vascular filter for endoluminally trapping emboli while simultaneously preserving vascular flow, vascular filter assemblies ("VFA's") known in the art include additional features including, for example, a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Note that a jugular approach necessitates that the VFA be introduced retrograde relative to the vector of blood flow within the vena cava, i.e., the VFA is introduced through the jugular vein and directed inferiorly toward an infrarenal position. Additionally, since the blood flow opposes the distal end of the VFA and passes toward the proximal end, the vena cava filter must open inferiorly such that its largest diametric section in apposition to the vessel walls opens toward the distal end of the VFA rather than toward the proximal end of the VFA as with the femoral approach.

The VFA may include fluid infusion ports positioned in the sidewall of the central access catheter to which the vascular filter is attached. Such fluid infusion ports may have a directional flow orientation such that any or all regions of the space delimited by the vena cava filter may be exposed to fluid flow therefrom.

The VFA may include proximal and distal ports disposed in the central access catheter and positioned entirely or partially distant from an open area bounded by the filter permit measuring pressure and/or flow velocity across the filter as a determinant of extent of capture of embolic material in the filter or for measuring flow rate at the position of the filter member as a positional indicator within the body. Such pressure and/or flow sensing may be accomplished by a hydrostatic fluid column in communication with each of the proximal and distal ports and a pressure transducer operably associated with a proximal end of the central access catheter.

The proximal and distal ports, and lumens associated therewith, may also provide means for introducing fluids, such as an anticoagulant, thrombolytic or other bioactive agents, contrast medium, blood transfusions, intravenous fluids or other medications. Alternatively, the proximal and distal ports may be used for withdrawal or evacuation of fluids or other material through the catheter. The multiple infusion ports also provide a means for introducing a flushing medium, such as saline, under elevated pressure to produce mechanical thrombolysis or induce thrombolysis by the infusion of thrombolytic agents directly to thrombus within the filter.

VFA's including the above-noted features are disclosed, for example, in Angel U.S. Patent Application Publication No. 2009/0062840 and Angel et al. U.S. Patent Application Publication No. 2010/0217304, both of which are hereby incorporated in their entirety herein. However, a need exists for a VFA including a self-expanding vascular filter attached to a catheter and constrained by a low profile sheath including a port passing through the sidewall of the sheath.

SUMMARY OF THE INVENTION

A VFA including a self-expanding vascular filter attached to a catheter and constrained by a low profile sheath including a port passing through the sidewall of the sheath benefits from dual use both as a central venous access catheter for administration of intravenous fluids, bioactive agents, contrast agents, flushing agents, pressurized fluids for mechanical thrombolysis and/or withdrawal of blood samples, and for capture of thrombus or emboli. Such a VFA further benefits from a low cross-sectional profile sheath defining an annular fluid delivery lumen in communication with the port passing through the sidewall for further delivery of fluid to the filter and release of pressure built up by the filter. Such a VFA including a dual-diameter sheath reduces trauma to a patient at the insertion point and enhances the patient's comfort.

In one aspect of the present invention, a vascular filter assembly includes a catheter body having a self-expanding filter member coupled thereto. A sheath is disposed directly over the self-expanding filter member such that the self-expanding filter member is at least partially constrained from expansion in a first configuration within an interior space defined between the sheath and the catheter body. The sheath includes at least one aperture disposed through a wall thereof.

In another aspect of the present invention, a vascular filter assembly includes a catheter body having a self-expanding filter member coupled thereto. A sheath is disposed directly over the self-expanding filter member such that the self-expanding filter member is at least partially constrained from expansion in a first configuration within an interior space defined between the sheath and the catheter body. The sheath includes at least one aperture disposed through a wall thereof. A proximally decreasing diametric taper is disposed in at least an outer diameter of the sheath proximal to the self-expanding filter member in the first configuration.

In a further aspect of the present invention, a vascular filter assembly includes a catheter body having a self-expanding filter member coupled thereto. A sheath is disposed directly over the self-expanding filter member such that the self-expanding filter member is at least partially constrained from expansion in a first configuration within an interior space defined between the sheath and the catheter body. At least one aperture is disposed through a wall of the sheath at a location proximal to the self-expanding filter member in the first configuration.

BRIEF DESCRIPTION OF THE DRAWINGS

FIG. 1 is a side elevational view of an embodiment of a vascular filter assembly in a first configuration.

FIG. 2 is a side elevational view of the vascular filter assembly of FIG. 1 in a second configuration.

FIG. 5 is a close-up view of the circled region marked 5 in FIG. 3.

FIG. 6 is a cross-sectional view of the close-up view of FIG. 5, taken generally along the lines 6-6 of FIG. 5 and illustrating an embodiment of a vascular filter assembly.

FIG. 7 is a cross-sectional view of the close-up view of FIG. 5, taken generally along the lines 6-6 of FIG. 5 and illustrating another embodiment of a vascular filter assembly.

FIG. 8 is a cross-sectional view of the close-up view of FIG. 5, taken generally along the lines 6-6 of FIG. 5 and illustrating a further embodiment of a vascular filter assembly.

FIG. 9A is a cross-sectional view of an embodiment of a vascular filter assembly taken generally along line 9-9 of FIG. 1.

The foregoing and other features and advantages of the invention are apparent from the following detailed description of exemplary embodiments, read in conjunction with the accompanying drawings; wherein like structural or functional elements may be designated by like reference numerals.

DETAILED DESCRIPTION OF THE PREFERRED EMBODIMENTS

Figure 3:
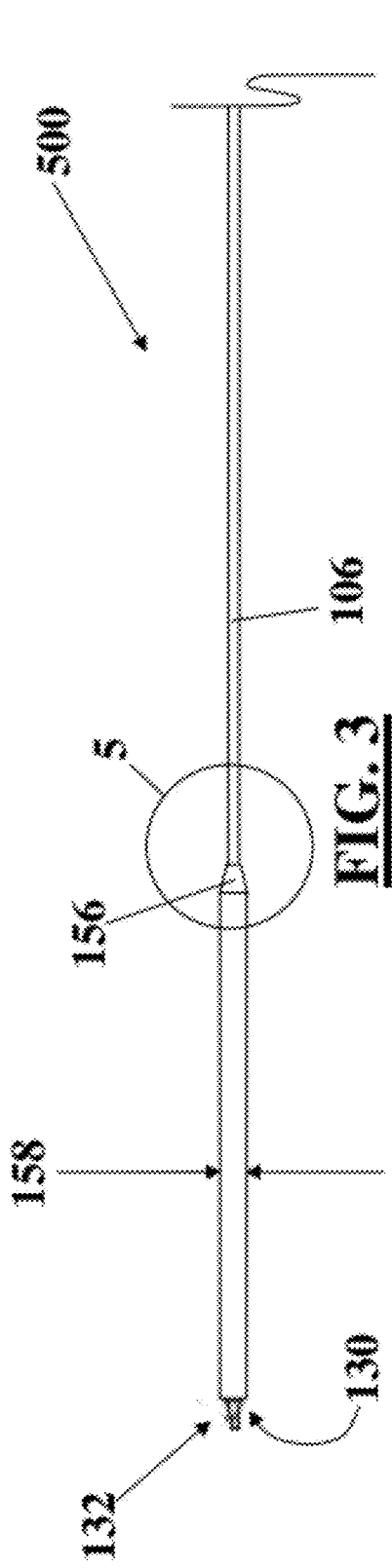
FIG. 3. is a close-up view of a distal end of the vascular filter assembly of FIG. 1 in a first configuration.

As used in this application, unless otherwise specifically stated, the terms "proximal" and "distal" are intended to refer to positions relative to a longitudinal axis of the VFA. Those skilled in the art will understand that the VFA has a distal end which is first inserted into a patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

The present invention may be configured for either a femoral approach or a jugular approach to the inferior vena cava. Vena cava filters are typically deployed infrarenaly, but may also be deployed suprarenaly. It will be understood that within the inferior vena cava blood flow is superior, i.e., toward a patients head. Thus, in all embodiments, the vena cava filter will be positioned so that it opens inferiorly, i.e., away from the patient's head and toward the direction of the blood flow. It will be appreciated, therefore, that in the present invention, the vena cava filter will have a different axial orientation on the central access catheter depending upon whether the device is intended for use in a femoral approach or a jugular approach.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Referring to FIGS. 1 and 2, in one embodiment, a vascular filter assembly ("VFA") 100 is illustrated in a first configuration 200 and a second configuration 300, respectively. The VFA 100 includes a catheter body 102 having a self-expanding filter member 104 coupled thereto. A sheath 106 is disposed directly over the filter member 104 and the catheter body 102 such that the filter member 104 is at least partially constrained from expansion in the first configuration 200. The filter member 104 is constrained from expansion within an interior space 108 (See FIGS. 6-9B) defined between the sheath 106 and the catheter body 102.

The filter member 104 may be slidably or fixedly attached to the catheter body 102 or may be removably coupled to the catheter body 102 for deployment as either a permanent filter or as a temporary and retrievable vena cava filter. Removable coupling of the filter member 104 to the catheter body 102 may be accomplished with a variety of release and retrieval mechanisms operably associated with the catheter body 102. Non-limiting examples of such release and retrieval mechanisms are disclosed, for example, in Angel U.S. Patent Application Publication No. 2009/0062840 and Angel et al. U.S. Patent Application Publication No. 2010/0217304.

Figure 9B:
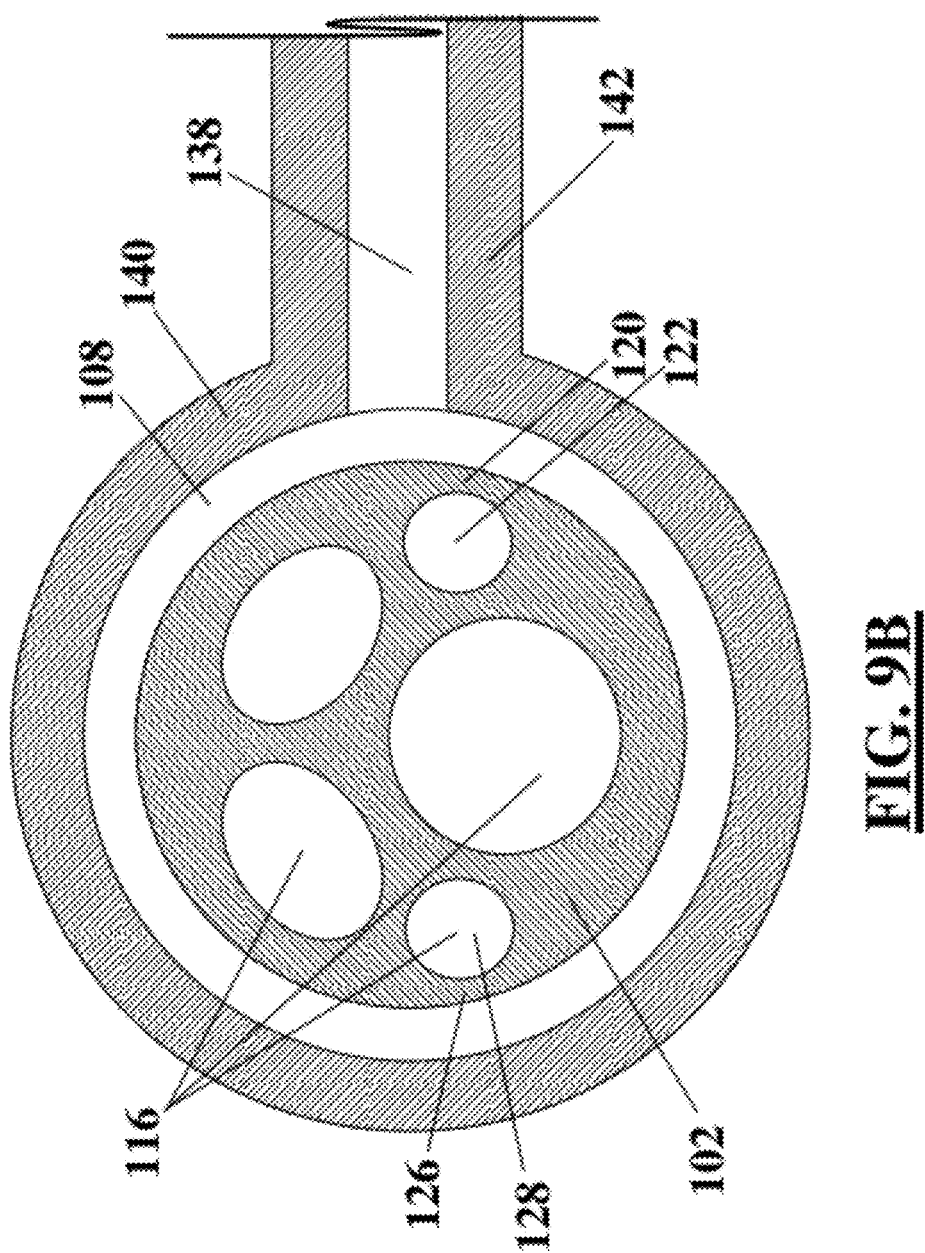
FIG. 9B is a cross-sectional view of another embodiment of a vascular filter assembly taken generally along line 9-9 of FIG. 1.

Referring to FIGS. 6, 7, and 9A, in one embodiment, the catheter body 102 comprises a single lumen 110. The single lumen 110 is in fluid communication with the interior space 108 via at least one port 112 disposed through the sidewall 114 of the catheter body 102. Referring to FIGS. 8 and 9B, in other embodiments, the catheter body 102 comprises multiple lumens 116. In one embodiment, the catheter body 102 includes at least one first port 118 disposed through a sidewall 120 thereof and providing fluid communication between the interior space 108 and a first lumen 122. The catheter body 102 further includes at least one second port 124 disposed through a sidewall 126 thereof and providing fluid communication between the interior space 108 and a second lumen 128. Bioactive agents, flushing fluids, pressurized mechanical thrombolytic fluids, or other fluids may be infused through the single lumen 110 or the first and second lumens 122, 128 and out of the at least one port 112, the at least one first port 118, and the at least one second port 124 to pass into the interior space 108 and ultimately into a patient's venous system for either local or systemic effect.

Again referring to FIGS. 1 and 2, the sheath 106 is concentrically disposed over the catheter body 102 such that relative longitudinal movement of the catheter body 102 and the sheath 106 (as indicated by arrows labeled M in FIG. 1) either exposes the filter member 104 in the second configuration 300 or captures the filter member 104 within the sheath 106 in the first configuration 200. The sheath 106 terminates in an annular opening 130 (corresponding to the interior space 108) at a distal end 132 thereof. A distal hub 134 is coupled to a proximal end 136 of the sheath 106.

Referring to FIGS. 1, 2, 9A and 9B, an infusion port 138 may be provided disposed through a sidewall 140 of the sheath 106. The infusion port 138 is adapted to receive a tube 142 that may include a luer or other type of fitting 144 at a proximal end thereof. The infusion port 138 provides fluid communication between an exterior of the distal hub 134 and the interior space 108, as illustrated in FIGS. 9A and 9B. The catheter body 102 extends through the distal hub 134 and passes through a lumen 146 (See FIGS. 6-8) of the sheath 106.

A proximal hub 148 is coupled to a proximal end 150 of the catheter body 102. The proximal hub 148 and the distal hub 134 are removably engageable with each other. A plurality of fluid lines, for example, fluid lines L1, L2, L3, L4, communicate with the proximal hub 148, as illustrated in FIGS. 1 and 2. Each of the fluid lines L1, L2, L3, and L4 is in fluid communication with at least one of the single lumen 110, the first and second lumens 122, 128, or other lumens within the catheter body 102. When the VFA is in the second configuration 300, the proximal and distal hubs 148, 134 may be removably engaged to form a hub assembly 152 that inhibits relative motion of the catheter body 102 and the sheath 106. Vascular filter assemblies and features thereof such as structure, orientation, and materials comprising the filter member 104, the sheath 106 and/or the catheter body 102 including single or multiple lumens that may be instructional or useful in the current application may be found in the disclosures of, for example, Angel U.S. Patent Application Publication No. 2009/0062840 and Angel et al. U.S. Patent Application Publication No. 2010/0217304.

Referring to FIGS. 5 and 6, in one embodiment of a VFA 400, the sheath 106 includes at least one aperture 154 disposed through the sidewall 140 thereof. In other embodiments, a plurality of apertures 154 is disposed through the sidewall 140 of the sheath 106. In another embodiment, the at least one aperture 154 is disposed through the sidewall of the sheath proximal to the filter member 104 in the first configuration 200.

Figure 4:
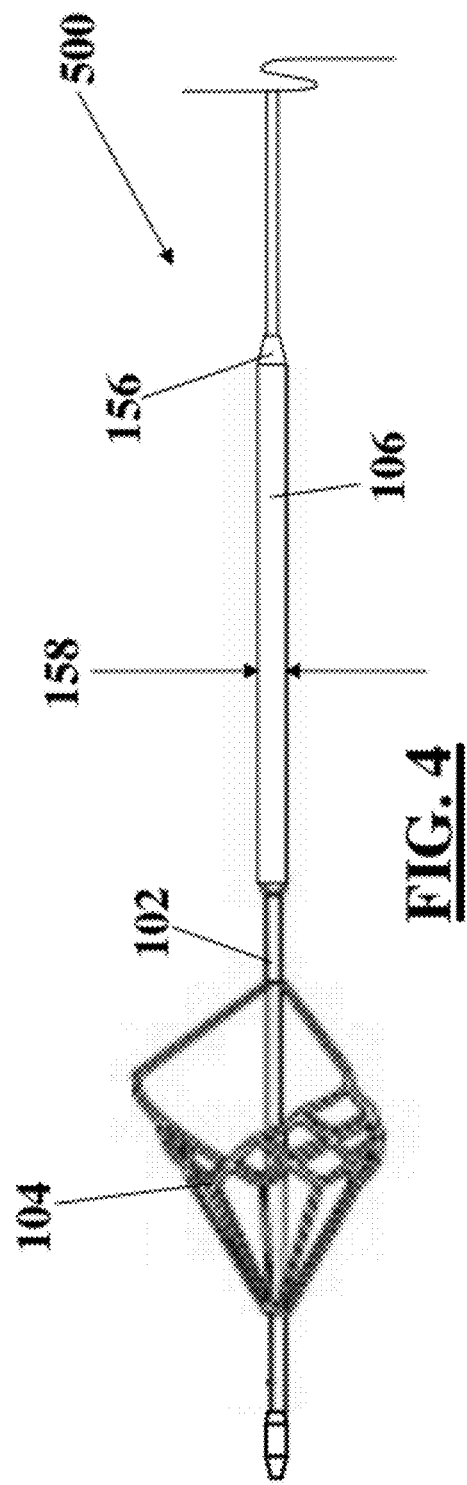
FIG. 4 is a close-up view of a distal end of the vascular filter assembly of FIG. 1 in a second configuration.

Referring to FIGS. 3 and 4, in one embodiment of a VFA 500, the sheath 106 includes a proximally decreasing diametric taper 156 disposed in at least an outer diameter 158 of the sheath sidewall 140. The proximally decreasing diametric taper 156 is disposed proximate to the filter member 104 when the VFA 500 is in the first configuration 200. Referring to FIG. 5, in one embodiment, the proximally decreasing diametric taper 156 is disposed proximal to the filter element 104 in the first configuration 200 and the at least one aperture 154 is disposed proximal or distal to the proximally decreasing diametric taper 156. Referring to FIGS. 5-8, in other embodiments, the proximally decreasing diametric taper 156 is disposed proximal to the filter element 104 in the first configuration 200 and the at least one aperture 154 is disposed proximal to the proximally decreasing diametric taper 156.

Referring to FIG. 6, the proximally decreasing diametric taper 156 is illustrated as disposed in the outer diameter 158 of the sheath sidewall 140. In this embodiment, the interior space 108 has about the longitudinal cross-sectional area measured anywhere longitudinally therealong in the first configuration 200. Of course, in the region of the filter member 104, the effective cross-sectional area of the interior space 108 is less due to the presence of the filter member 104.

It is contemplated that any buildup of pressure within a fluid infused through the interior space 108 caused by the presence of the filter member 104 therein may be alleviated by providing the fluid an additional escape path through the at least one aperture 154. Such an escape path may not only provide pressure relief, but may also provide a path for the infused fluid into a patient's venous system for either local or systemic effect. Further, referring to FIG. 6, it is contemplated that a flow rate of fluid that can be infused into the patient's venous system through the interior space 108 in the presence of the at least one aperture 154 may be comparable to a flow rate of fluid that can be infused through a similarly sized interior space 108 lacking the filter member 104 within in a sheath 106 lacking the at least one aperture 154.

Referring to FIG. 7, the proximally decreasing diametric taper 156 is illustrated as disposed in both an interior diameter 160 and the outer diameter 158 of the sheath sidewall 140. In this embodiment, the interior space 108 accommodating the self-expanding filter member 104 in the first configuration has a larger cross-sectional area than the interior space 108 proximal to the filter member 104 in the first configuration 200. The larger cross-sectional area is provided by an increased internal diameter 162 of the sheath 106 proximate to the filter member 104 in the first configuration 200 as compared to an internal diameter 164 of the sheath 106 proximal to the filter member 104 in the first configuration 200.

Referring to FIG. 8, the proximally decreasing diametric taper 156 is illustrated as disposed in both the interior diameter 160 and the outer diameter 158 of the sheath sidewall 140. In this embodiment, the sheath sidewall 140 is thinner proximal to the proximally decreasing diametric taper 156 than distal to the proximally decreasing diametric taper 156. Similar to the taper geometry illustrated in FIG. 7, the interior space 108 accommodating the self-expanding filter member 104 in the first configuration has a larger cross-sectional area than the interior space 108 proximal to the filter member 104 in the first configuration. The larger cross-sectional area is provided by an increased internal diameter 162 of the sheath 106 proximate to the filter member 104 in the first configuration 200 as compared to an internal diameter 166 of the sheath 106 proximal to the filter member 104 in the first configuration 200.

With regard to FIGS. 7 and 8, it is contemplated that any buildup of pressure within a fluid infused through the interior space 108 caused by the presence of the filter member 104 therein may be alleviated by providing the fluid an additional escape path through the at least one aperture 154 and also by providing the enlarged interior space 108 defined by the increased internal diameter 162. The additional escape path and larger cross-sectional area of the interior space 108 proximate the filter member 104 may cooperate to not only provide pressure relief, but to also provide paths for the infused fluid into a patient's venous system for either local or systemic effect. Further, referring to FIGS. 7 and 8, it is contemplated that a flow rate of fluid that can be infused into the patient's venous system through the interior space 108 having an enlarged cross-sectional area defined by the increased internal diameter 162 of the sheath 106 proximate to the filter member 104 and in the presence of the at least one aperture 154 is comparable to a flow rate of fluid that can be infused through the interior space 108 having a longitudinally uniform cross-sectional area defined by the increased internal diameter 162 but lacking the filter member 104 and the at least one aperture 154.

While the present invention is not limited to specific dimensional sizes of either the catheter body 102, the sheath 106, any lumen diameter or port dimension, an exemplary outer diameter size of the sheath 106 distal to the proximally decreasing diametric taper 156 is between about 8 Fr (2.7 mm) and about 9 Fr (3.0 mm) and an exemplary outer diameter size of the sheath 106 proximal to the proximally decreasing diametric taper 156 is between about 6 Fr (2.0 mm) and about 8 Fr (2.7 mm). An exemplary outer diameter size of the catheter body 102 is between about 4 Fr (1.3 mm) and 7 Fr (2.4 mm). An exemplary diametric dimension of the at least one aperture 154, for example the diameter of a circular aperture, is between about 0.002 inch and about 0.02 inch. In an embodiment having a plurality of apertures 154, each of the apertures 154 may have the same or a different diametric dimension; however, an exemplary average diametric dimension for the plurality of apertures 154 is between about 0.002 inch and about 0.02 inch.

Lumen diameter and port dimension are a function of design requirements and are variable depending upon the desired purpose and function of the lumen or port, e.g., pressure sensing, infusion, evacuation, guidewire, flow sensing, or flow conduit. The plurality of apertures 154 may comprise any number of apertures as desired, for example, the plurality of apertures 154 may include as few as 2 apertures or as many apertures as can be fit onto the sheath 106.

In use, an introducer sheath is first placed into the body in a normal manner for introducing a central venous line, such as by the Seldinger technique. Specifically, after accessing a vein using a large bore needle, under local anesthesia, a guidewire is inserted through the needle bore and passed into the vein. Once the guidewire is positioned, the needle is withdrawn, and a dilator together with the introducer sheath are introduced over the guidewire. Once the introducer sheath is positioned at a desired location within the venous system under, for example, radiography, the dilator may be removed from the patient. Radiopaque markers associated with the introducer sheath may be employed to assist in positional visualization of the distal end of the introducer sheath. The VFA is maintained in the first configuration while introducing the VFA into the introducer sheath. The sheath 106 constrains the filter member 104 during its passage through the introducer sheath and positioning of the distal end of the VFA within the patient's vasculature. Once the distal end of the VFA reaches the distal end of the introducer sheath, the filter member 104 is deployed.

If filter therapy alone is desired, the filter member 104 is detached from the catheter body 102 and the catheter body 102, introducer sheath, and guidewire are withdrawn from the patient. Where both central venous access and filter therapy is desired, the introducer sheath and catheter body 102 with the filter member 104 are left in the patient until withdrawal is required.

A vascular filter assembly ("VFA") including a self-expanding filter member attached to a catheter body and constrained from expansion in a first configuration by a low profile constraining sheath is presented. The low profile constraining sheath facilitates introduction of the VFA through a vessel to a site of treatment within a patient. The VFA further benefits from having at least one aperture disposed through a sidewall of the low profile constraining sheath to alleviate blockage of infusion fluid by the filter member.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the vascular filter assembly described herein and to teach the best mode of carrying out the same.

What is claimed is:

1. A low profile vena cava filter assembly, consisting of:
    a. an elongate flexible catheter body having a self-expanding vena cava filter member concentrically coupled thereto about a distal portion of the catheter body;
    b. an outermost sheath having a substantially uniform inner diameter along a longitudinal length of the sheath such that the self-expanding vena cava filter member is in a constrained position within and bound by the inner diameter of the outermost sheath and a proximal section of the outermost sheath having a first wall thickness and a distal section of the outermost sheath having a second wall thickness greater than the first wall the distal section being movably disposed over the self-expanding vena cava filter member and the catheter body such that the self-expanding vena cava filter member is at least partially constrained from expansion in the constrained position by the second wall thickness of the distal section of the outermost sheath and within an interior space defined by the inner diameter of the distal section of the sheath, wherein the proximal section of the outermost sheath includes at least one aperture disposed through a wall thereof, the at least one aperture being proximal to the distal section of the outermost sheath and only in the proximal section;
    c. a distal hub member fixedly attached to a proximal end of the outermost sheath such that an infusion port disposed on the distal hub provides fluid communication between an exterior of the distal hub and the interior space defined between the sheath and the catheter body in the first configuration;
    d. a proximal hub member fixedly attached to the catheter body in a second configuration such that the proximal and distal hubs form a hub assembly with an infusion port that provides fluid communication between an exterior of the hub assembly and the interior space defined between the sheath and the catheter body, wherein the proximal hub member and the distal hub member are removably engageable with and longitudinally translatable relative to each other along a longitudinal axis of the vascular filter assembly; and
    e. a plurality of fluid lines in fluid communication with the proximal hub.

2. The low profile vascular filter assembly of claim 1, wherein the outermost sheath slides longitudinally relative to the catheter body from the first configuration to a second configuration to release the self-expanding vena cava filter member from being constrained within the outermost sheath.

3. The low profile vascular filter assembly of claim 2, wherein each of the plurality of fluid lines is in fluid communication to a corresponding lumen of a plurality of lumens longitudinally disposed within the catheter body and substantially parallel to each other in a non-coaxial manner.

4. The low profile vascular filter assembly of claim 3, wherein the catheter body comprises at least one sidewall having an aperture such that at least one of the corresponding lumens of the catheter body is in fluid communication with the interior space defined between the outermost sheath and the catheter body.

5. The low profile vascular filter assembly of claim 1 wherein, the outermost sheath has a tapered section configured to decrease the wall thickness from the distal end of the outermost sheath to proximal end of the outermost sheath.

6. The low profile vascular filter assembly of claim 5, wherein the outermost sheath has an outer diameter less than or equal to about 9 French proximal to the tapered section.

7. The low profile vascular filter assembly of claim 6, wherein the outermost sheath has an outer diameter less than or equal to about 8 French proximal to the tapered section.

8. The low profile vascular filter assembly of claim 7, wherein the outermost sheath has an outer diameter less than or equal to about 7 French proximal to the tapered section.

* * * * *